United States Patent [19]

Ryu

[11] 4,119,677
[45] Oct. 10, 1978

[54] TITANIUM TETRACHLORIDE AS HETEROGENEOUS CATALYST FOR TRANSALKYLATION OF ALKYLAROMATIC HYDROCARBONS

[75] Inventor: Ji-Yong Ryu, Des Plaines, Ill.

[73] Assignee: UOP Inc., Des Plaines, Ill.

[21] Appl. No.: 789,583

[22] Filed: Apr. 21, 1977

Related U.S. Application Data

[62] Division of Ser. No. 644,783, Dec. 29, 1975, Pat. No. 4,048,247.

[51] Int. Cl.$^2$ ............................ C07C 3/62; C07C 5/28
[52] U.S. Cl. ............................... 260/672 T; 260/668 A
[58] Field of Search ......................... 260/672 T, 668 A

[56] References Cited

U.S. PATENT DOCUMENTS

| | | | |
|---|---|---|---|
| 2,834,821 | 5/1958 | Bergsteinsson | 260/672 T |
| 2,999,074 | 9/1961 | Bloch et al. | 252/441 |
| 3,354,078 | 11/1967 | Miale et al. | 260/672 T |
| 3,637,881 | 1/1972 | Williams et al. | 260/668 A |
| 3,720,726 | 3/1973 | Mitsche et al. | 260/672 T |

FOREIGN PATENT DOCUMENTS 1,044,490  9/1966  United Kingdom ............... 260/672 T

*Primary Examiner*—Delbert E. Gantz
*Assistant Examiner*—C. E. Spresser
*Attorney, Agent, or Firm*—James R. Hoatson, Jr.; John G. Cutts, Jr.; William H. Page, II

[57] ABSTRACT

A process for the conversion of aromatic hydrocarbons is disclosed which is especially useful for reaction of an alkylating agent, preferably propylene, with an aromatic hydrocarbon. Novel feature is use of a catalyst system comprising TiCl$_4$ and a Group III-A metal oxide.

6 Claims, No Drawings

TITANIUM TETRACHLORIDE AS HETEROGENEOUS CATALYST FOR TRANSALKYLATION OF ALKYLAROMATIC HYDROCARBONS

CROSS REFERENCE TO RELATED APPLICATION

This application is a division of my prior, copending application Ser. No. 644,783 filed Dec. 29, 1975, now U.S. Pat. No. 4,048,247, Sept. 13, 1977.

BACKGROUND OF THE INVENTION

1. Field of the Invention

The present invention relates to an improved process for the conversion of an aromatic hydrocarbon in the presence of a titanium tetrachloride catalyst system.

The invention will be described with reference to alkylation, i.e., the synthesis of cumene by alkylation of benzene with propylene in the presence of the catalyst, but will find use in alkylaromatic transalkylation and isomerization as well.

2. Description of the Prior Art

Conversion of aromatic hydrocarbons is well known in industry. Some of the aromatic conversion reactions which occur include alkylation of aromatic hydrocarbons with an alkylating agent such as an olefin, disproportionation of alkylaromatic hydrocarbons and isomerization of alkylaromatic hydrocarbons such as xylenes.

Of special interest, has been the propylation of benzene to cumene. Cumene is used for the production of phenol and acetone. Cumene is also dehydrogenated to form methylstyrene, in a process similar to that used to convert ethylbenzene to styrene. Cumene is also used as a blending component in aviation gasoline because of its high octane number. The consumption of cumene in the U.S.A. was about 350,000 metric tons in 1968. Of this total, 94% was used for the production of phenol or acetone.

It is well known that cumene can be synthesized from benzene and propylene using a catalyst of $AlCl_3$, SPA or $BF_3$. SOA is a generally accepted abreviation for solid phosphoric acid catalyst, or phosphoric acid which is absorbed on kieselguhr or other support.

$AlCl_3$ is a very popular alkylation catalyst, because of its high activity. Unfortunately, the catalyst operates as a slurry or sludge which is messy to handle on a commercial scale, and also is corrosive. The highly reactive nature of this Friedel-Crafts metal halide catalyst, $AlCl_3$, is desirable when attempting to alkylate benzene with ethylene, because less active catalyst systems do not work. However, for alkylation with propylene such highly reactive systems are not necessary.

The $AlCl_3$ catalyst, although not equivalent to a Ziegler-Natta catalyst, is similar, at least for some olefin reactions. $AlCl_3$ will promote polymerization of both ethylene and propylene, and alkylation of benzene with both ethylene and propylene. These catalysts also promote transalkylation of alkyl groups. This is in contrast to slightly less active systems, such as SPA catalyst, which catalyzes alkylation of benzene with propylene, but does not catalyze transalkylation satisfactorily.

Another highly selective catalyst system has been developed for the alkylation of benzene with olefins. This catalyst comprises boron trifluoride. The boron trifluoride catalyst system is exceptionally active and permits operation with dilute olefin streams, but it requires the continuous addition of $BF_3$ to maintain catalyst activity. High catalyst activity also leads to oligomerization of olefins, so contact time of olefins with $BF_3$ catalyst should be as short as possible. This catalyst is also exceptionally water sensitive, as water not only destroys the catalyst, but produces very corrosive solutions which attack downstream processing units. $BF_3$ also frequently appears in the product, and must be removed therefrom.

Because of the interest in alkylating benzene with olefins, and because of the inadequacies of existing catalyst systems, I studied the work that others had done, and made exhaustive investigations to determine if it would be possible to find a catalyst which would have the activity and selectivity required to produce an acceptable cumene product, while making maximum use of existing petroleum resources.

A highly active catalyst was sought, to permit operation at lower temperatures with less utility cost, cost of construction, and to operate with less catalyst. In new units this would mean smaller, and cheaper reactor vessels, while in existing units it would mean that an increase in capacity could be obtained by changing catalyst in an existing reactor vessel, with minor modifications.

High selectivity is necessary, not only to permit operation with feedstreams which are not 100% pure olefin, but also to maximize production of the desired product, and to minimize production of polymerized olefins, or polyalkylated aromatic compounds.

Accordingly, many catalyst systems were studied to find a catalyst with excellent activity and selectivity, which was not corrosive or destroyed by water.

There has been extensive work done with Ti catalysts, though most work occurred in conjunction with studies of Ziegler-Natta catalysts. The closest prior art known is U.S. Pat. No. 2,381,481 (Class 260-683.15), U.S. Pat. No. 2,951,885 (Class 260-671), U.S. Pat. No. 2,965,686 (Class 260-671) and U.S. Pat. No. 3,153,634 (Class 252-429).

In U.S. Pat. No. 2,381,481, preparation and use of a catalyst prepared by treating alumina gel with fluotitanic acid is disclosed. This catalyst is used for polymerization of olefins to heavier hydrocarbons, and also for alkylation of paraffins with olefins, the latter when operating at high temperatures, between 700° and 900° F. or higher. No mention is made of alkylation of aromatics with olefinic hydrocarbons or transalkylation of polyalkylbenzenes.

In U.S. Pat. No. 2,951,885, there is disclosed the use of titanium trihalide on activated alumina or other activated acidic oxide for alkylation of benzene with olefins. The catalyst is originally a tetrachloride, subsequently reduced to the trichloride with an alkali metal such as sodium, lithium, or potassium. The examples show that this catalyst will alkylate benzene with ethylene.

In U.S. Pat No. 2,965,686, the thrust of the application was to develop a titanium subchloride catalyst. In Example II, a reaction between cumene and propylene was disclosed using titanium tetrachloride catalyst. The catalyst in Example II was tetrachloride. The catalyst was prepared by activating alumina by evacuation at a temperature of 600 C. for an unspecified period of time. The resultant catalyst was then used in an alkylation reaction for the propylation of cumene to form diisopropylbenzene. This patent is silent as to the type of alumina which was used as the base for the catalyst.

In U.S. Pat. No. 3,153,634, there is disclosed the use of titanium subhalides in a polymerization reaction. The patentee is probably describing a catalyst for production of solid polymer products. On page 3 lines 65–75, the patentee mentions use of benzene as an inert solvent to hold dissolved olefins, rather than as a reactant.

Accordingly, work continued on developing an improved process for the catalytic conversion of aromatic hydrocarbons.

Accordingly, the present invention provides a process for the catalytic conversion of an aromatic hydrocarbon comprising contacting the aromatic hydrocarbon with a reactant at aromatic hydrocarbon conversion conditions in the presence of a catalyst system comprising titanium tetrachloride and alumina wherein the catalyst system is prepared by passing $TiCl_4$ vapor over activated alumina at a temperature of 20 to 400 C. for 1 to 10 hours.

The catalyst used comprises titanium tetrachloride impregnated on an activated metal oxide which possesses surface hydroxyl groups. Specific examples of these metal oxides will include the Group III-A metal oxides which possess surface hydroxyl groups and which also possess a relatively high surface area such as alumina, gallium oxide, indium oxide, and thallium oxide. Of these compounds, the preferred substrate is alumina, and especially low density, high surface area aluminas such as gamma-alumina or, if so desired, eta-alumina.

The apparent bulk density of the alumina may range from about 0.3 to about 0.7 $g/cm^3$ or higher with a surface area ranging from about 1 to about 500 $m^2/g$. The alumina may be in any shape, one example of the substrate being spheroidal alumina which is prepared by the conventional and commercial oil-drop method as described in U.S. Pat. No. 2,610,314. In addition, it is also contemplated within the scope of this invention that the alumina may be treated to provide greater physical stability, one type of treatment being to impregnate the gamma-alumina with a compound such as barium nitrate, which, upon calcination, is converted into barium oxide. The latter compound will then, as hereinbefore set forth, provide greater physical stability for the alumina. It is also contemplated within the scope of this invention that a commercial gamma-alumina may also be used as the support. However, since this commercial gamma-alumina could contain an excessive amount of water which would consume an excess of titanium tetrahalide without any beneficial effect on the catalyst, in the preferred embodiment of this invention the commercial gamma-alumina is subjected to a pre-drying step by heating to a temperature in the range of from about 400 to about 550 C. under an inert gas or hydrogen flow for a period of about 1 to about 8 hours.

In order to achieve the maximum activity of the metal oxide support, it is necessary to avoid severe drying of said support. For example, the drying of alumina at temperatures in excess of about 600 such as 650, under vacuum, will seriously deplete the alumina of the hydroxyl groups present thereon. This severe drying step will not only remove the water which is absorbed on the alumina, but will also remove the aforesaid surface hydroxyl groups which are essential to make an active catalyst, said surface hydroxyl groups reacting with the titanium component of the titanium tetrachloride.

The gamma-alumina which has been predried according to the above paragraph is then placed in an appropriate apparatus which may comprise a flask, tube, etc., and a gas mixture of nitrogen and titanium tetrachloride which has been prepared by bubbling nitrogen gas through the liquid titanium tetrachloride at room temperature is passed over the gamma-alumina at temperatures of 25 to 135. Thereafter the temperature is increased to 550 or more. The passage of the nitrogen-titanium tetrachloride mixture over the alumina is effected about 0.5 to 10 hours or more, the time being dependent upon the amount of gamma-alumina which is present and the flow rate of the titanium tetrachloride-nitrogen gas mixture. It is preferred to pass the titanium tetrachloride or the gaseous mixture over the support at a temperature of about 25 to about 135. The temperature is then raised to 250 or a desired temperature, either gradually or in a series of steps. The preferred temperature for the heat treatment of this resulting composite is from about 135 to about 550, however, it will be dependent on the temperature which is used in the aromatic hydrocarbon conversion process. Generally, it is preferred that the temperature which is used in the treatment of the composite be equal to, or higher than, the aromatic hydrocarbon conversion temperature. Thereafter the temperature is maintained at this point and a stream of nitrogen is passed over the catalyst composite for an additional period which may range from about 1 to 10 hours. At the end of this time, the finished catalyst is then sealed under an inert atmosphere such as argon, helium, nitrogen, etc., prior to being used.

Alternatively, the catalyst may be prepared by forming a solution of titanium tetrachloride in a polar, non-aqueous organic solvent and impregnating the alumina. Thereafter the impregnated alumina is then treated under a nitrogen flow at temperatures in the range hereinbefore set forth. After subjecting the impregnated substrate to these temperatures for a predetermined period of time, the finished catalyst is also recovered and maintained under an inert atmosphere until use thereof.

It is believed that the important factor in the thermal treating steps is the temperature, rather than the total time, as long as the total period for thermal treatment is reasonably long; around five or six hours. It is believed that the activity of the catalyst is effected by the thermal treatments because the thermal treatments desorb water molecules from the catalyst surface. Water can compete for active sites with the reactants, thus water is to some extent a catalyst poison. However, if catalyst deactivation occurs due to water adsorption, the catalyst can be regenerated by appropriate further thermal treatment under inert gas flow. Any regenerative thermal treatments should probably approximate those of the original thermal treatments, in that heating which is too rapid, or to too high a temperature, may cause hydrolysis of the $TiCl_4$ component on the catalyst, which would reduce catalyst activity. Another danger of a rapid high temperature catalyst regeneration would be the formation of corrosive gases and liquids due to rapid evolution of $H_2O$ vapor and chlorine compounds.

It is also contemplated within the scope of this invention that the catalyst system hereinbefore described may, if so desired, be composited on a solid support. The preferred solid supports which may be utilized comprise high surface area inert compounds, some representative examples of which will include silica, magnesia or mixtures of silica with other inorganic oxides such as silica-zirconia, silica-thoria, silica-magnesia-zirconia, etc., charcoal, coal, diatomaceous earths and clays such as fuller's earth, bentonite, montmorillonite, kieselguhr, etc. It is to be understood that these compounds will act only as supports for the catalyst system and will not enter into the catalytic activity of the composite. The catalyst system comprising titanium tetrachloride composited on the Group IIIA metal oxide and the inert support may be composited in any manner known in the art such as by impregnation, deposition, rolling, mixing, etc.

In addition, it is also to be considered within the scope of this invention that one or more promoters may be added to the catalyst system. It is believed that use of one or more promoters selected from the metals of Group VIB or Group VIII of the Periodic Table may be beneficial to the practice of the present invention.

At least about 0.5 weight percent titanium, on an elemental basis, is believed necessary for a significant amount of reaction to occur. The upper limit on titanium is believed to be about 20 wt. %.

When it is desired to use the catalyst system in an alkylaromatic isomerization process, then alkylaromatic isomerization reaction conditions should be used. Reaction conditions are disclosed in U.S. Pat. No. 3,637,881 (Class 260-668a), the teachings of which are incorporated by reference. When it is desired to use the catalyst system of the present invention for alkylaromatic transalkylation then appropriate reaction conditions should also be used. These are disclosed in U.S. Pat. No. 3,720,726 (Class 260-672t), the teachings of which are incorporated by reference. Reaction conditions for the alkylation of aromatic hydrocarbons will be discussed in detail in a latter part of this specification.

The catalyst may be disposed in a reactor vessel as a fixed fluidized or moving bed of catalyst. The reactants may contact the catalyst in upflow, downflow or crossflow fashion, though upflow of reactants over a fixed bed of catalyst is preferred.

The liquid hourly space velocity in the reactor may range from 0.1 to 20. Because catalyst of the present invention is very active for the alkylation reaction, significantly higher space velocities are possible than when using some prior art catalysts, e.g., SPA. To some extent, the liquid hourly space velocity is related to temperature in the reaction zone, in general, a higher LHSV will require higher temperature operation.

The ratios of reactants and other reaction conditions which occur when alkylating benzene with light olefins, and preferably are basically those well known in the art. Pressures may range from 1 to 100 atmospheres, or even higher. It is desirable to maintain pressures high enough to have a liquid phase in the reaction zone. Although it is possible to operate at very high pressure, little advantage is gained thereby, in fact, an increase in pressure seems to have a harmful effect. Preferred pressure seems to be around 20 to 60 atm, with an optimum pressure of about 35 atm.

Temperature effects both the conversion and selectivity of the reaction. Temperature may range between ambient and 250. At very low temperatures, the catalyst is not sufficiently active to permit the desired reaction to proceed at a satisfactory rate. At very high temperatures, it is believed that the catalyst may be damaged, by formation of carbonaceous materials on the catalyst.

If the reaction is kinetically controlled, an increase in temperature should increase the rate of reaction. As a general statement, this is true, but the temperature dependence may not be as large as expected, if the reaction is limited by mass transport of reactants and products to and from the catalyst surface. Preferred operating temperature is probably about 100 to 200 C.

The catalyst may be disposed in a reactor vessel as a fixed, fluidized or moving bed of catalyst. The reactants may contact the catalyst in upflow, downflow or crossflow fashion, though upflow of reactants over a fixed bed of catalyst is preferred. The liquid hourly space velocity in the reactor may range from 0.1 to 20. However, higher LHSV is possible depending on the desired conversion level of propylene. Because catalyst of the present invention is believed very active for the alkylation reaction, significantly higher space velocities should be possible than when using some prior art catalysts, e.g., SPA. To some extent, the liquid hourly space velocity is related to temperature in the reaction zone, in general, a higher LHSV will require higher temperature operation.

EXAMPLE I

In this example a catalyst was prepared by predrying 125 cc of gamma-alumina at a temperature of 550° C. for a period of six hours under a flow of 2000 cc/min. nitrogen gas. Thereafter a gaseous mixture of nitrogen and titanium tetrachloride which was prepared by bubbling nitrogen gas through liquid titanium was passed over the gamma-alumina at a temperature of 75° C. for a period of 40 minutes. The flow rate of nitrogen was 2000 cc/min. At the end of this time, the temperature was increased to 250° C. while maintaining the nitrogen-titanium tetrachloride vapor flow over the gamma-alumina. The nitrogen-titanium tetrachloride flow was discontinued and the catalyst composite was treated with a nitrogen flow for a period of 4.4 hours while maintaining the temperature at 250° C. At the end of this period, the catalyst was analyzed and found to contain 2.17% titanium and 4.86% chlorine.

ILLUSTRATIVE EMBODIMENT I

The reaction contemplated is alkylation of benzene with propylene. Catalyst is maintained as a fixed bed, of 50 cc volume. Reactants are passed upflow over the catalyst bed. Benzene is dried by circulating it over high surface area sodium. Pure propylene is dried by passing it over type 4-A molecular sieves. Benzene and propylene are mixed together and charged to the reactor. The reaction is carried out at 120 to 245 C., 1 to 3 LHSV, and at 25 to 55 atmospheres pressure. The reactor is started up full of liquid benzene and then the mixture of propylene and benzene added. It is believed that if propylene alone is charged, or even propylene and benzene charged simultaneously, high molecular weight polymer may form. Using the conditions indicated above, a high yield of cumene is expected.

I claim as my invention:

1. A process for the transalkylation of an alkylaromatic hydrocarbon which comprises contacting the alkylaromatic hydrocarbon at transalkylation conditions with a catalyst system consisting essentially of titanium tetrachloride on an activated Group III-A metal oxide having surface hydroxyl groups, said catalyst system having been prepared by passing $TiCl_4$ vapor with an inert gas over said metal oxide at a temperature of 20° C. to 400° C. for 1 to 10 hours and thereafter thermally treating the resultant $TiCl_4$-containing oxide in an inert atmosphere at a temperature of from about 135° C. to about 550° C.

2. The process of claim 1 wherein the alkylaromatic hydrocarbon is toluene.

3. The process of claim 1 wherein the alkylaromatic hydrocarbon is ethylbenzene.

4. The process of claim 1 wherein the Group III-A metal is oxide is alumina.

5. The process of claim 4 wherein the alumina is gamm-alumina.

6. The process of claim 1 wherein the catalyst contains, on an elemental basis, about 0.5 to about 20 wt. % titanium.

* * * * *